United States Patent [19]

Ndife

[11] Patent Number: 5,248,502
[45] Date of Patent: Sep. 28, 1993

[54] METHOD FOR DECREASING THE ALLERGENICITY OF PSYLLIUM SEED HUSK BY ALKALINE TREATMENT

[75] Inventor: Louis I. Ndife, Columbus, Ohio

[73] Assignee: Kellogg Company, Battle Creek, Mich.

[21] Appl. No.: 789,309

[22] Filed: Nov. 8, 1991

[51] Int. Cl.$^5$ ............................................. A61K 35/78
[52] U.S. Cl. .............................. 424/195.100; 514/885; 514/892
[58] Field of Search ...................... 424/195.1; 514/885, 514/892

[56] References Cited

U.S. PATENT DOCUMENTS

| | | | |
|---|---|---|---|
| 4,813,613 | 7/1988 | Salete | 241/7 |
| 4,958,140 | 9/1990 | Pflaumer | 424/439 |
| 5,009,916 | 4/1991 | Colliopoalos | 426/615 |
| 5,015,486 | 5/1991 | Franssell | 426/243 |

*Primary Examiner*—John W. Rollins

[57] ABSTRACT

A method of reducing the allergenicity of psyllium seed husk. Psyllium seed husk is treated with a alkaline solution at a temperature and for a time sufficient to reduce the allergenicity of the psyllium seed husk.

20 Claims, No Drawings

METHOD FOR DECREASING THE ALLERGENICITY OF PSYLLIUM SEED HUSK BY ALKALINE TREATMENT

BACKGROUND OF THE INVENTION

1. Field of the Invention

The present invention relates to a novel method for decreasing the allergenicity of psyllium seed husk.

2. Discussion of the Background

Psyllium is a known mucilaginous material which has been used extensively in bulk laxatives. More recently, psyllium has been found to have a hypocholesterolemic effect if ingested by humans and lower animals.

The source of psyllium is the seeds from the plants of the Plantago genus, which grows in certain sub-tropical regions. The seeds are dark brown, smooth, boat-shaped and shiny. Since it is believed by those skilled in the art that the active ingredient of psyllium is the psyllium seed gum, which is located primarily in the seed husk, present technology uses the ground seed husk as the source for psyllium.

Generally, integral psyllium seeds are coarsely ground with crude grinding equipment in India and sub-tropical regions where the psyllium seeds originate in an attempt to separate the outermost husk material from the underlying pigmented seed coat layer of the psyllium seeds. In this crude grinding process, particles of various size from these layers end up mixed with one another as a function of the grinding process. Because of the type and condition of the grinding equipment and variability in the physical dimensions of the psyllium seeds themselves, it is common to have discrete pieces of the seed coat mixed in with the husk material.

Various methods and apparatus for obtaining high purity mucilage or husk material from psyllium seeds have been proposed. For example, U.S. Pat. No. 4,813,613 discloses complex apparatus for producing powdered psyllium seed husk including a plurality of impact grinding steps.

Psyllium compositions have been incorporated into food products for many years. For example, U.S. Pat. No. 4,950,140 discloses a method of incorporating psyllium into cookie compositions containing flours, sugars, oils, etc. U.S. Pat. No. 5,015,486 discloses dry mixes for the preparation of baked goods, particularly muffins which contain psyllium. U.S. Pat. No. 5,009,916 discloses psyllium containing dietary aids.

A psyllium seed comprises a substantially centrally located germ, an endosperm surrounding the germ, a relatively thin colored seed coat (bran) surrounding the endosperm, and a husk surrounding the colored seed coat. It has now been discovered that the seed coat material from psyllium seeds, in general, is high in specific protein fractions which contain allergens. As noted above, it is common to have discrete pieces of the seed coat material mixed in with coarsely ground psyllium seed husk. The present invention provides a novel, convenient and simple method for treating coarsely ground psyllium seed husk to decrease the allergenicity of the psyllium seed husk. The method of the present invention provides a means for decreasing the allergenicity of psyllium seed husk without requiring size reduction of the coarsely ground psyllium seed husk or physical separation of the coarsely ground psyllium seed husk into fractions of different particle size.

SUMMARY OF THE INVENTION

Accordingly, one object of the present invention is to provide a method for selectively decreasing the allergenicity of psyllium seed husk compositions without substantially altering the psyllium seed husk foodstuff qualities.

It is a further object of the present invention to provide a method for altering the molecular structure and/or chemistry of the allergen-containing fractions of psyllium seed coat material found in coarsely ground psyllium seed husk.

Additional objects and advantages of the present invention will become apparent from the following detailed description and examples.

The present invention relates to a novel method for treating ground psyllium seed husk to reduce its allergenicity. In accordance with the present invention, ground psyllium seed husk is treated with an alkaline solution at a temperature of about 40°-70° C. This process is applicable for process/production scale-up at a psyllium husk handling facility, as well as for smaller applications.

DETAILED DESCRIPTION OF THE INVENTION

The method of the present invention comprises treating coarsely ground psyllium seed husk with an alkaline solution at a temperature of about 40°-70° C. After being subjected to the alkaline treatment in accordance with this invention, the psyllium seed husk exhibits selectively decreased allergenicity and remains suitable for use as a food additive or as an ingredient of a food additive or food product.

Psyllium husk compositions typically contain many complex biochemical components in the husk, seed coat, etc., which are present in the psyllium composition. Surprisingly, the present method allows one to substantially reduce the allergenicity of these psyllium compositions without generating toxic decomposition products. Further, the present process allows one to reduce allergenicity and yet retain the food additive or food product qualities of the psyllium husk composition.

According to the inventive method, psyllium seed husk, including but not limited to coarsely ground psyllium seed husk, is mixed with an aqueous alkaline solution in a weight/volume ratio of psyllium seed husk to alkaline solution of from about 2 g/100 ml to about 20 g/100 ml. If the ratio of psyllium seed husk to alkaline solution is below about 2 g/100 ml, the psyllium seed husk slurry will be very thin and it will be very difficult to completely dry the psyllium seed husk after treatment. If the ratio of psyllium seed husk to alkaline solution is above about 20 g/100 ml, the psyllium seed husk may not be wholly and completely wetted by the alkaline solution. Obviously, weight/volume ratios above and below 2-10 g/100 ml may be used in the present process to reduce the allergenicity of psyllium seed husk. However, weight/volume ratios from about 2-20 g/100 ml provide preferred processing conditions for the process of the present invention.

Preferably, the psyllium seed husk to alkaline solution ratio is between about 5 g/100 ml and about 10 g/100 ml. Most preferably, the psyllium seed husk to alkaline solution ratio is about 5 g/100 ml.

The alkaline solution used to treat the ground psyllium seed husk can be any one of many known alkaline solutions. The alkaline solution can be prepared by dissolving a salt in water so as to obtain an alkaline solution. Any salt which produces an alkaline solution upon dissolution may be used in the present process. Such salts include carbonates, bicarbonates, oxides, hydroxides, etc. Generally, alkali and alkaline earth metal salts will be used in the present process. Examples of suitable carbonates and bicarbonates include sodium, potassium and calcium carbonates and bicarbonates. Examples of particularly suitable hydroxides are sodium hydroxide, potassium hydroxide, magnesium hydroxide, and calcium hydroxide. Bases previously used in the food industry are especially suitable.

The alkaline treatment of the present invention is conducted at an alkalinity (referred to herein as a normality (N) of the alkaline solution or the pH of the alkaline solution), for a sufficient time and at a suitable temperature so as to reduce the allergenicity of the psyllium seed husk. These variables of time, temperature and alkalinity are interrelated and are variable within the scope of the present invention so long as the treatment condition is sufficient to reduce the allergenicity of the psyllium seed husk. For example, when the treatment temperature is relatively high, the treatment time can be shortened for a given alkalinity. Similarly, use of a more alkaline solution allows one to reduce the treatment temperature and treatment time so long as the allergenic proteins are effectively decomposed. Longer treatment times may be used for dilute alkaline solutions and shorter treatment times for more concentrated alkaline solutions. One skilled in the art can vary the alkalinity, time and temperature combinations so as to obtain a psyllium product having reduced allergenicity.

The allergenicity of psyllium seed husk treated by the process of the present invention can be determined by methods known in the art. As noted above, specific proteins in the psyllium seed are allergens. The allergenicity of the treated psyllium product can be determined by extracting protein from the treated psyllium product and then determining the allergenicity of the extracted proteins by known electrophoresis and immunoblotting techniques (H. A. Sampson and S. K. Cooke, *J. Am. Coll. Nutrition*, 9(4):410-417, John Wiley & Sons, Inc. (1990)). Immunoblotting allows one to determine the extent of IgE antibody binding to specific psyllium proteins, providing a measure of the allergenicity of psyllium protein fractions. One skilled in the art can readily utilize these known techniques to evaluate specific treatment conditions to determine adequate temperature, time and alkalinity to achieve the desired reduction in allergenicity.

The alkaline solution has a pH of between about 8 and 14, preferably between 10 and 12, and most preferably about 12. The normality of the alkaline solution is generally about 0.1N-0.5N for the weight/volume ratios of psyllium seed husk to alkaline solution set forth above. Of course, those skilled in the art will understand that the ratio of psyllium seed husk to alkaline solution can be modified for alkaline solutions of different normality. As discussed above, for the higher alkalinity solutions (0.5N and higher) the treatment time may be shortened so long as one allows sufficient time for the psyllium to adequately make contact with the alkaline solution. Treatment with alkaline solutions having a normality of about 0.5N are generally conducted for about 10-30 minutes. The use of solutions with higher alkalinity contributes to corrosion of processing equipment.

The psyllium seed husk/alkaline solution mixture is then maintained at a temperature between about 40°-70° C., preferably between about 58° and about 62° C. for a time period of about 10-60 minutes, preferably about 40-50 minutes. The psyllium seed husk/alkaline solution mixture is more preferably maintained at a temperature of about 60° C., for about 45 minutes. Temperatures below 40° C., may be used in the present process provided that the treatment time is sufficiently long. Although the alkaline treatment process of the present invention is operable at these low temperatures and longer treatment times, such processing conditions are inconvenient and not economical. Treatment above about 70° C. may also be used, however one should avoid temperatures at which undesirable decomposition products are formed. For example, under the alkaline conditions noted above, higher temperatures result in racemization of the amino acids of psyllium proteins from the L-form to the D-form. The D-amino acids have little or no nutritional value and some are toxic. Other undesirable amino acid residues such as lysinylalanine are also formed. Accordingly, temperatures high enough to form these protein decomposition products should be avoided in the present process.

After the psyllium seed husk has been treated with the alkaline solution as described above, the psyllium seed husk has a substantially decreased allergenicity. The alkaline solution-treated psyllium seed husk is dried by any suitable means to produce psyllium seed husk having reduced allergenicity. Suitable drying methods are well-known in the art.

The dried psyllium seed husk, which exhibits significantly decreased allergenicity as compared to the initial ground psyllium seed husk, is then ready for use for any known purpose of psyllium seed husk, and is especially useful as an ingredient of a food additive and/or food product. The dried psyllium seed husk treated to reduce allergenicity according to the present invention has an allergenicity which is reduced by 30-100% relative to untreated dried psyllium seed husk. Preferably, the treated psyllium seed husk has an allergenicity which has been reduced by 60-100% relative to the untreated product.

As described above, the psyllium seed husk subjected to the alkaline treatment process in accordance with the present invention is preferably coarsely ground psyllium seed husk. Typically, commercially available coarsely ground psyllium seed husk will have a purity of about 70 wt. %—about 95 wt. %, preferably at least about 80 wt. %. Obviously, the process of the present invention may be used to treat both impure coarsely ground psyllium seed husk, as well as more highly refined psyllium products having a purity of 85 wt. %-98 wt. % and even in excess of 99 wt. % psyllium seed husk.

The alkaline treatment of the inventive method is effective in the treatment of ground psyllium seed husk of very low purity and can also be applied to other materials containing the psyllium seed husk allergen-containing protein fractions in order to reduce the allergenicity of these other psyllium materials.

The process of the present invention may be applied to ground psyllium seed husk of varying purity, as well as compositions containing psyllium seed husk, allergen-containing protein fractions. These compositions may contain flours, brans, seeds, cracked seeds, etc., in addition to the psyllium seed husk. The additional materials present in the composition may be non-allergenic or may be allergenic themselves. The process of the present invention functions to reduce the allergenicity of the psyllium seed husk present in the composition and, concurrently, reduces the allergenicity which may be present in the other components of the composition. For example, treatment of a composition containing psyllium seed husk and peanut flour will reduce the allergenicity of the psyllium seed husk protein fractions, as well as the allergenicity of the peanut flour proteins.

The present invention is useful in reducing the allergenicity of psyllium seed husk of varying purity. The present invention is also useful in reducing the allergenicity of compositions containing an allergenic psyllium seed husk material. The psyllium seed husk which is obtained by the present process may be utilized to prepare conventional dietary and food compositions containing psyllium.

Other features of the invention will become apparent in the course of the following description of an exemplary embodiment which is given for illustration of the invention and is not intended to be limiting thereof.

EXAMPLE

Psyllium seed husk of decreased allergenicity was produced as follows.

Five grams of a highly allergenic fraction of coarsely ground psyllium seed husk (about 80 wt. % purity) was mixed with 100 ml of 0.1N sodium hydroxide (NaOH) to produce a 5% slurry of psyllium seed husk. The slurry was made by mixing the coarsely ground psyllium seed husk and the 0.1N NaOH in a Hobart Mixer for 3 to 5 minutes to uniformly mix the psyllium seed husk and the alkaline solution and to ensure that all particles of the psyllium seed husk were wetted. The psyllium seed husk slurry was then poured into a 600 ml beaker, covered with aluminum foil, and incubated in a water bath at a temperature of 60° C. for 45 minutes. At the end of the 45 minute incubation at 60° C., the psyllium seed husk slurry was poured into a metal tray, dried and tested to determine its allergenicity. The above procedure was repeated three times using NaOH solutions of 0.05N, 0.025N and 0.0N, respectively, as the alkaline solution. The 0.0N NaOH solution acted as a control.

The psyllium seed husk treated as set forth above with 0.1N NaOH, 0.05N NaOH, 0.025N NaOH and 0.0N NaOH (control) were evaluated for their allergy-evoking response or allergenicity on a scale of 0 to 3, 0 being the lowest allergenicity rating and 3 being the highest allergenicity rating. The allergenicity scale is based on the relative intensity of stained (e.g., amido black staining) psyllium protein fractions obtained by immunoblotting with IgE and/or IgG antibodies specific for psyllium protein fractions. The psyllium seed husk treated with 0.1N NaOH had an allergenicity rating of 0. The psyllium seed husk treated with 0.05N NaOH had an allergenicity rating of 1. The psyllium seed husk treated with 0.025N NaOH had an allergenicity rating of 2. Finally, the psyllium seed husk treated with the control (distilled water) had an allergenicity rating of 3.

These results demonstrate that psyllium seed husk of greatly reduced allergenicity is produced by the alkaline treatment of the present invention.

By processing psyllium seed husk or other psyllium seed material in accordance with the present invention, the health related benefits possible from ingesting psyllium can be achieved without the deleterious and disadvantageous allergenic response associated with the ingestion of psyllium.

Obviously, numerous modifications and variations of the present invention are possible in light of the above teachings. It is therefore to be understood that within the scope of the appended claims, the invention may be practiced otherwise than as specifically described herein.

I claim:

1. A method of reducing the allergenicity of psyllium seed husk comprising: treating coarsely ground psyllium seed husk with an alkaline solution to form a slurry thereof; and heating the slurry for a time and to a temperature sufficient to reduce the allergenicity of said psyllium said husk.

2. The method of claim 1, wherein said alkaline solution is an aqueous solution of an alkali or alkaline earth metal carbonate, bicarbonate, oxide or hydroxide.

3. The method of claim 1, wherein said alkaline solution is an aqueous solution of an alkali or alkaline earth metal hydroxide.

4. The method of claim 1, wherein said alkaline solution is an aqueous sodium hydroxide or potassium hydroxide solution.

5. The method of claim 1, wherein said alkaline solution has a normality of about 0.1-0.5N.

6. The method of claim 1, wherein said treating step is conducted for about 10-60 minutes at a temperature of about 40°-70° C.

7. The method according to claim 6, wherein the weight/volume ratio of psyllium seed husk to alkaline solution is from about 5 g/100 ml to about 10 g/100 ml.

8. The method of claim 1, wherein the psyllium seed husk is treated with the alkaline solution by mixing coarsely ground psyllium seed husk with said alkaline solution in a weight/volume ratio of psyllium seed husk to alkaline solution of between about 2 g/100 ml and about 20 g/100 ml.

9. The method of claim 8, wherein the weight/volume ratio of psyllium seed husk to alkaline solution is from about 5 g/100 ml to about 10 g/100 ml.

10. The method of claim 1 wherein the alkaline solution has a pH of 10 to 12.

11. A method of reducing the allergenicity of psyllium seed husk comprising the steps of coarsely grinding psyllium seeds and recovering ground psyllium seed husk therefrom; mixing the ground psyllium seed husk with an alkaline solution to produce a psyllium seed husk slurry; and then heating the psyllium seed husk slurry for a time and at a temperature sufficient to reduce the allergenicity of the psyllium seed husk.

12. The method of claim 11, wherein said alkaline solution is an aqueous solution of an alkali or alkaline earth metal carbonate, bicarbonate, oxide or hydroxide.

13. The method of claim 11, wherein said alkaline solution is an aqueous solution of an alkali or alkaline earth metal hydroxide.

14. The method of claim 11, wherein said alkaline solution is an aqueous sodium hydroxide or potassium hydroxide solution.

15. The method of claim 11, wherein said alkaline solution has a normality of about 0.1-0.5N.

16. The method of claim 11, wherein said treating step is conducted for about 10-60 minutes at a temperature of about 40°-70° C.

17. The method of claim 11, wherein the coarsely ground psyllium seed husk is treated with the alkaline solution by mixing the coarsely ground psyllium seed husk with the alkaline solution in a weight/volume ratio of psyllium seed husk to alkaline solution of between about 2 g/100 ml and about 20 g/100 ml.

18. The method of claim 11 wherein the alkaline solution has a pH of 10 to 12.

19. A psyllium seed husk having reduced allergenicity, prepared by the process of claim 1.

20. A psyllium seed husk having reduced allergenicity prepared by the process of claim 11.

* * * * *